Dec. 14, 1948. W. A. BENTON ET AL Plant Pat. 815
ENGLISH OR PERSIAN WALNUT TREE
Filed Feb. 11, 1947
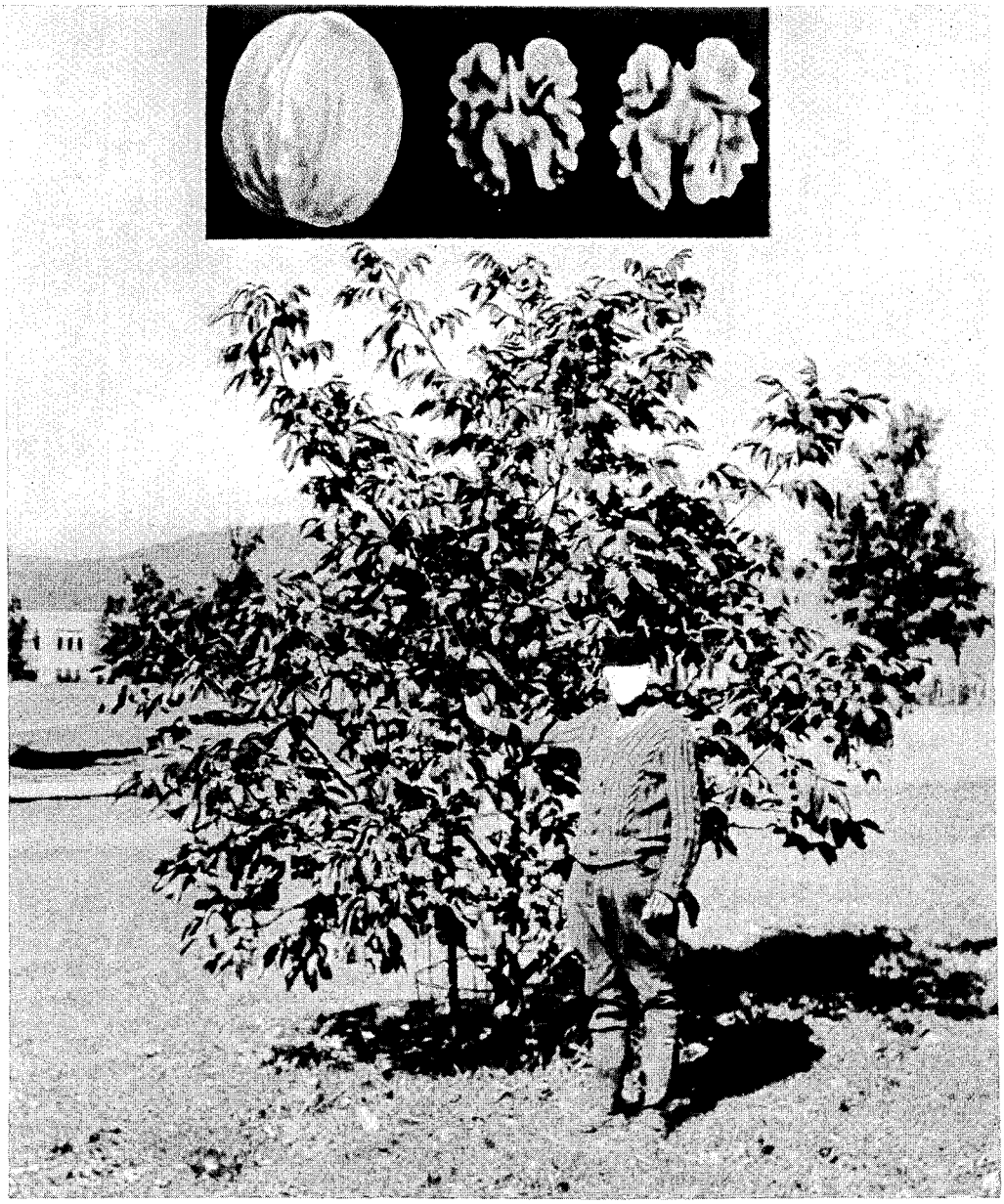
William A Benton and Gilbert L. Smith
Inventors
James H. Littlepage
Attorney Patented Dec. 14, 1948 Plant Pat. 815

UNITED STATES PATENT OFFICE

815

ENGLISH OR PERSIAN WALNUT TREE

William A. Benton and Gilbert L. Smith,
Wassaic, N. Y.

Application February 11, 1947, Serial No. 727,783

1 Claim. (Cl. 47—62)

This invention relates to a new variety of walnut tree and more particularly, to a variety of English or Persian walnut tree of the Carpathian type or strain.

The object of this invention is to provide a new and hardy variety of walnut tree for the North which will resist, and even thrive with rapid growth, cold climatic conditions and yet produce large, thin shelled nuts of relatively early ripening characteristics.

These and other objects will be apparent from the following specification and photographs which illustrate, in the inset, a whole walnut and two kernels, extracted from another similar nut, and a tree of seven season's growth, all of the new variety.

The new variety is a selected one raised from a planting of nuts purchased from the Wisconsin Horticultural Society in the spring of 1935. In the spring of 1938, a graft from the selected seedling was put on a black walnut stock, a small one having been set in the fall previous. The graft first bore pistillate blossoms in the spring of 1942, again in the spring of 1943, and in the spring of 1944 it also bore staminate blossoms. After pollinizing the pistillate blossoms, twelve nuts were produced, one whole nut and the kernels of another being illustrated in the inset. The photograph of the tree was taken in the fall of 1944, the outline of a six-foot man being shown beside the tree for comparison.

The grafts from this variety are vigorous and rapid growers, and have made good trees in practically all observed cases. The tree illustrated was subjected to —34 degrees F. in February of 1943 and neither this nor a similar graft on lower ground was injured, whereas a Broadview Persian walnut graft of similar age and within fifty feet of the illustrated tree was killed back to within six inches of the graft union; that is, back to the five-year-old wood.

Thus, the tree is rapid-growing, vigorous, and very hardy. The shape of the head is medium upright; the branching characteristics are medium to dense, with crotch angles medium to wide. Trends towards several long terminals in the top of the tree have been observed so that more spreading of the branches should reasonably be expected of the tree as it becomes older.

The trunk bark is medium to slick, light gray in color with slightly greenish cast. The leaves are large and glossy, the leaflets being of medium erectness and medium to dark green color, with no red coloring at the petioles.

The twigs are medium thick, slightly crooked at the nodes and of greenish brown color. The lenticels are sparse to medium.

Normally there is one prominent bud, although sometimes two occur. These buds are of medium size, closely separated, and, in shape, medium to short, round, and not much contracted. The catkins are medium in length and compactness, borne quite profusely. As for the flower bracts, they are medium.

Observations were taken in the town of Amenia, county of Dutchess, State of New York, about two and one-half miles south of the Wassaic post office.

The illustrated nuts are elliptical, of medium length, with apexes flattened bilaterally and depressed centers, while the bases are round and fairly blunt. The shells are light brown, with shallow grooves running lengthwise crossed by shallower grooves, thus causing a somewhat netted appearance of the surface which, in general, is fairly smooth, although a few slight pits occur near the suture.

The nuts are thin shelled, having shallow, narrow sutures which remain closed until cracked. The partitions are very thin and do not hang to the kernels, the latter being very wrinkled, medium to light in color, and of medium oiliness. Two kernels together, taken from a good sized nut, were $1\frac{5}{16}$ inches long, $1\frac{1}{16}$ inches wide, and $\frac{11}{16}$ inch thick.

The characteristics of a green husk are: smooth, medium green color, medium thickness. The husk cracks open before the nut drops from the tree and sometimes drops with the nut, although sometimes the nut drops from the husk. In either instance, the hull separates freely and cleanly from the nut.

The ripening date, in normal years, is about September 15th at Wassaic, New York. This is about two weeks before the earliest black walnuts ripen under similar conditions.

In general, the nuts are quite uniform in size, averaging approximately $1\frac{11}{16}$ inches long, $1\frac{3}{8}$ inches wide, and $1\frac{5}{16}$ inches thick.

The first pistillate blossoms from which the nuts were produced appeared receptive about May 19, 1944, and all appeared receptive by May 24, 1944. The nuts started to fall from the tree by September 15, 1944, after a ripening period of 114 to 119 days.

Having now described the parentage and dominant characteristics of the new variety, what we claim is:

The variety of walnut tree herein shown and described characterized by its resistance to cold climatic conditions, and production of relatively large early ripening nuts.

WM. A. BENTON.
GILBERT L. SMITH.

REFERENCES CITED

The following references are of record in the file of this patent:

UNITED STATES PATENTS

| Number | Name | Date |
|---|---|---|
| Pl. Pt. 494 | Schafer | Dec. 16, 1941 |